US 6,572,535 B2

(12) United States Patent
Watanabe et al.

(10) Patent No.: US 6,572,535 B2
(45) Date of Patent: Jun. 3, 2003

(54) ENDOSCOPE

(75) Inventors: Atsushi Watanabe, Hino (JP); Hideo Ito, Akishima (JP); Michio Sato, Hachioji (JP); Hidenobu Kimura, Hachioji (JP); Takayasu Miyagi, Hachioji (JP); Tae Nakatsuji, Hachioji (JP); Ryuichi Toyama, Hachioji (JP); Kan Naito, Hachioji (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 10/091,862

(22) Filed: Mar. 6, 2002

(65) Prior Publication Data

US 2002/0128537 A1 Sep. 12, 2002

(30) Foreign Application Priority Data

Mar. 12, 2001 (JP) ........................................ 2001-069105

(51) Int. Cl.7 ................................................. A61B 1/00
(52) U.S. Cl. ........................ 600/117; 600/130; 600/424
(58) Field of Search ................................ 600/114, 117, 600/118, 130, 424

(56) References Cited

U.S. PATENT DOCUMENTS

| 4,805,595 | A | * | 2/1989 | Kanbara .................... 600/140 |
| 5,807,241 | A | * | 9/1998 | Heimberger ................ 600/142 |
| 5,840,024 | A | | 11/1998 | Taniguchi et al. |
| 6,432,041 | B1 | * | 8/2002 | Taniguchi et al. .......... 600/118 |

FOREIGN PATENT DOCUMENTS

JP 2000-93386 4/2000

\* cited by examiner

*Primary Examiner*—John Mulcahy
(74) *Attorney, Agent, or Firm*—Scully, Scott, Murphy & Presser

(57) ABSTRACT

An endoscope includes an insertion section inserted into the body cavity and a probe provided inside the insertion section for detecting the form of the endoscope. The probe includes a plurality of coil portions arranged in the longitudinal direction of the insertion section of the endoscope and a wire electrically connecting the coil portions. The coil portions and the wire are covered with a flexible member. And the outer diameter of the covered wire is smaller than the outer diameter of the covered coil portions.

24 Claims, 11 Drawing Sheets

ENDOSCOPE

CROSS-REFERENCE TO RELATED APPLICATIONS

This application is based on and claims priority of Japanese Patent Application No. 2001-69105 filed on Mar. 12, 2001, the contents of which are incorporated herein by reference.

BACKGROUND OF THE INVENTION

1. Field of the Invention

This invention relates to an endoscope that allows an operator to observe the form of an inserted part of the endoscope through detection of the magnetic filed generated by magnetic field generating coils placed inside of the insertion section of the endoscope by an endoscope form detecting apparatus.

2. Description of the Related Art

Generally, the insertion section of an endoscope comprises, from the proximal end, a tubular section, a curving section and a distal end structural section. The tubular section is elongate and flexible. The distal end section contains an optical system for illumination and an optical system for observation.

When an operator inserts the insertion section into a body lumen, he or she controls the curving section to bend following the curve of the lumen while he or she gradually inserts the insertion section into the deep portion of the body lumen.

When the lumen that the insertion section is inserted into has complicated curves, like a colon or a small intestine, it is difficult for the operator to know how the curving section bends.

To know the form of the insertion section during the operation, Japanese Patent Laid-Open Publication No. 2000-93386 discloses an endoscope that has a probe with a plurality of magnetic coils placed along the axial direction of the endoscope to generate magnetic fields, these coils are for detecting the form of the insertion section. This endoscope generates an image signal representing the form of the insertion section by detecting the magnetic fields generated by each of the coils using an apparatus located outside of the endoscope, and sends the image signal to a display to show the form of the inserted section.

However, the probe for detecting the form of the insertion section placed inside of the endoscope has a rather large outer diameter. Because of this large diameter, the endoscope having the probe inside tends to have a high contents filling rate at the cross-section area of the insertion section tube. The contents filling rate is a rate of the total cross-section area of all contents of a tube per a cross-section area of inside of the tube at predetermined part of the tube. The term "contents" covers all objects inside of the tube. For example, the contents may include optical lenses for an optical observation system, CCD camera for detecting an image taken by the optical lenses and signal lines of the CCD camera which run toward a proximal portion in the insertion portion. The contents may also include optical fibers running from a proximal portion of the insertion section to a distal portion of it that directs illuminating light to the distal end of the insertion section. The contents may also include an air/water supply tube for supplying air and water to the distal portion of the insertion section. The air/water supply tube comprises a nozzle and a tube, the tube is connected to the nozzle and runs toward the proximal part of the insertion section.

An air/water supply channel branch is a part where the air/water supply channel is connected to an air supply channel and a water supply channel to fluidly communicate with each other. Because the air/water supply channel branch has a large volume, when it is placed inside of the insertion section, the contents filling rate of this part will be locally high. Therefore, the contents are pressed by one another and the friction rate among the contents is increased. In such a situation, the movements of the contents are hampered, and the durability of the endoscope is decreased.

In many cases, the tubular section, which is a part of the insertion section, has a spiral tube in the innermost layer. The spiral tube is formed of a spirally wound metal tape. This spiral tube has gaps of predetermined width between each wind of the metal tape. The curving section, which is also a part of the insertion section, has a curving tube in the innermost layer. The curving tube is formed of many short cylindrical tubular bodies rotatably jointed each other in series. This curving tube has gaps of predetermined width between each cylindrical tubular body. As the probe has a larger outer diameter at the coil portions, if the coil length in a longitudinal direction is shorter than the gap width of the spiral tube or the gap width of the bendable section, the coil portions of the probe will engage into these gaps. This engagement may prevent the probe to move smoothly in the longitudinal direction, and damage may the probe or the other contents.

In view of the forgoing, an object of the invention is to provide an endoscope having a good durability.

SUMMARY OF THE INVENTION

The present invention provides an endoscope. The endoscope comprises an insertion section for being inserted into the body cavity; a probe provided inside said insertion section for detecting the form of said endoscope. The probe includes a plurality of coil portions arranged in the longitudinal direction of said insertion section of said endoscope, a wire electrically connecting said plurality of coil portions and a flexible member covering said coil portions and said wire. The cross section area of said covered wire is smaller than the cross section area of said covered coil portions.

Furthermore, an endoscope of the present invention comprises an insertion section for being inserted into the body cavity; a probe provided inside said insertion section for detecting the form of said endoscope. The probe includes a plurality of coil portions arranged in the longitudinal direction of said insertion section of said endoscope, a wire electrically connecting said plurality of coil portions and a flexible member covering said coil portions and said wire. The cross section area of said covered wire is smaller than the cross section area of said covered coil portions. A device is located outside the body, for detecting the magnetic field generated from said probe or for generating the magnetic field to be detected by said probe. A processor is provided for calculating the form of said endoscope insertion section on the basis of the magnetic field detected by said probe or said outside device. A monitor is provided for displaying the form of said endoscope insertion section on the basis of a result calculated by said processor.

BRIEF DESCRIPTION OF THE DRAWINGS

The accompanying drawings, which are incorporated in and constitute a part of the specification, illustrate exemplary embodiments of the invention, and together with the general description above and the detailed description of illustrative embodiments given below, serve to explain the principles of the invention.

FIG. 14 illustrates a sectional constitution of a coil portion of a form detecting probe.

FIG. 15 illustrates another sectional constitution of a coil portion of a form detecting probe.

FIG. 16 illustrates a further sectional constitution of a coil portion of a form detecting probe.

DETAILED DESCRIPTION

A first embodiment of the present invention is now explained with reference to FIGS. 1 to 8.

Figure 1:
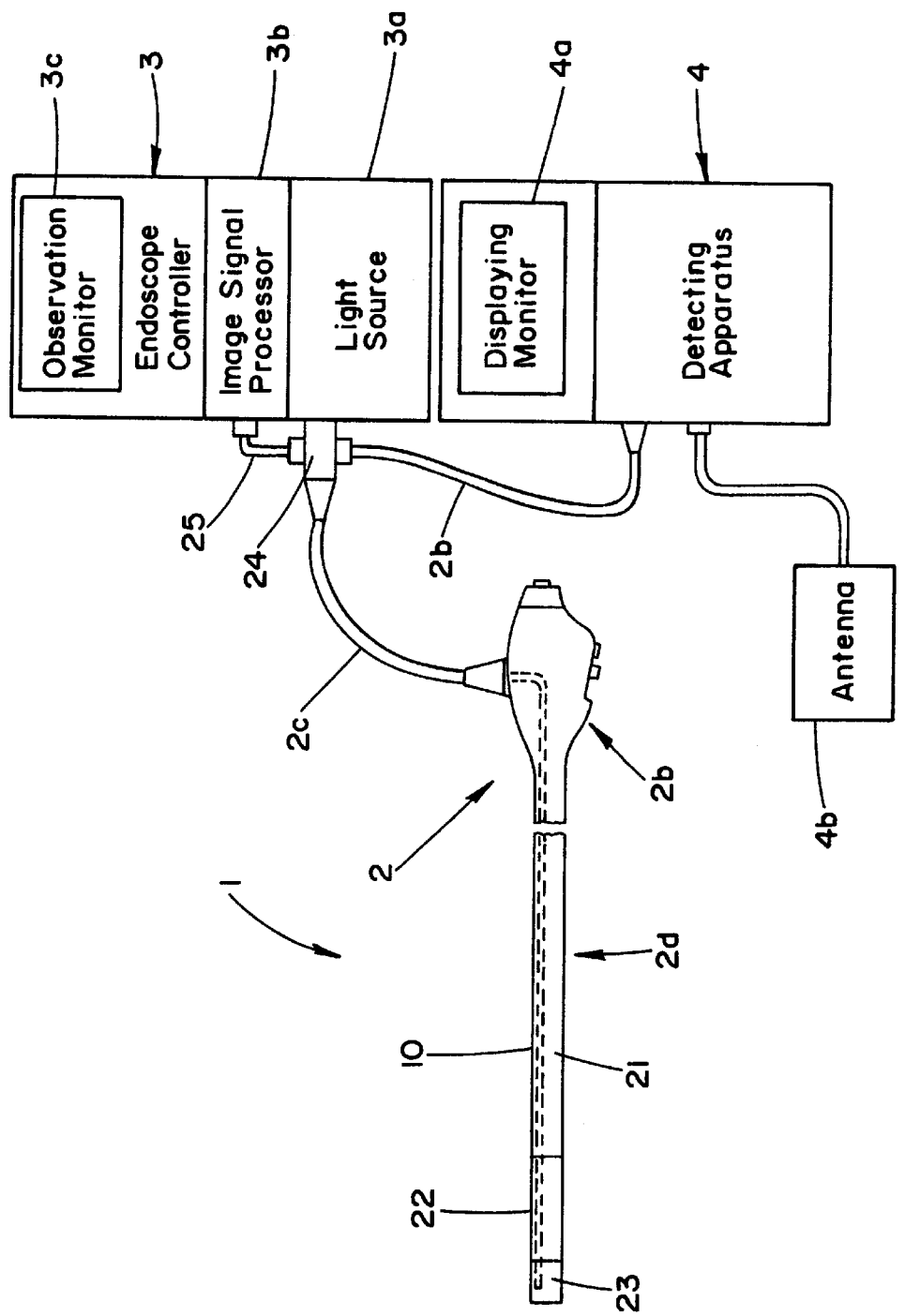
FIG. 1 illustrates a schematic view of an endoscope system according to a first embodiment of the present invention.

As shown in FIG. 1, an endoscope system 1 comprises an endoscope 2 and an endoscope controller 3 and an endoscope form detecting apparatus 4. The endoscope 2 comprises an insertion section 2a, inside of which a form detecting probe is provided along the whole length thereof. The endoscope controller 3 comprises a light source 3a including an illuminating lamp (not shown) to supply light to the endoscope 2, an image signal processing section 3b including a signal processing circuit (not shown), an observation monitor 3c for displaying images obtained by the endoscope 2. The endoscope form detecting apparatus 4 comprises a form displaying monitor 4a for displaying the form of an insertion section of the endoscope 2 and a signal processing circuit (not shown). The endoscope form detecting apparatus 4 is also connected to an antenna 4b for detecting the magnetic field generated from the insertion form detecting probe 10.

The above-mentioned endoscope 2 includes an elongate insertion section 2a to be inserted into a body cavity, an operation section 2b which is located on a proximal portion of the insertion section 2a and is also held by an operator, and a universal cord 2c extending from one side of the operation section 2b.

The above-mentioned insertion section 2a comprises an elongate flexible tubular section 21, a curving section 22 located on the distal end side of the flexible tubular section 21, and a distal end structural section 23 having hard structure located on the distal end side of the curving section 22. The flexible tubular section 21, and the curving section 22, and the distal end structural section 23 are arranged, respectively, from the proximal end of the insertion section 2a to a distal end thereof.

A connector 24 detachably connects to the light source 3a is provided on the proximal end portion of the universal cord 2c. A first connecting cable 25 is detachably connected to one side of the connector 24. The first connecting cable 25 is also connected to the image signal processor 3b of the endoscope controller 3. Moreover, a second connecting cable 26 is detachably connected to the other side of the connector 24. The second connecting cable 26 is also connected to the endoscope form detecting apparatus 4.

Figure 2:
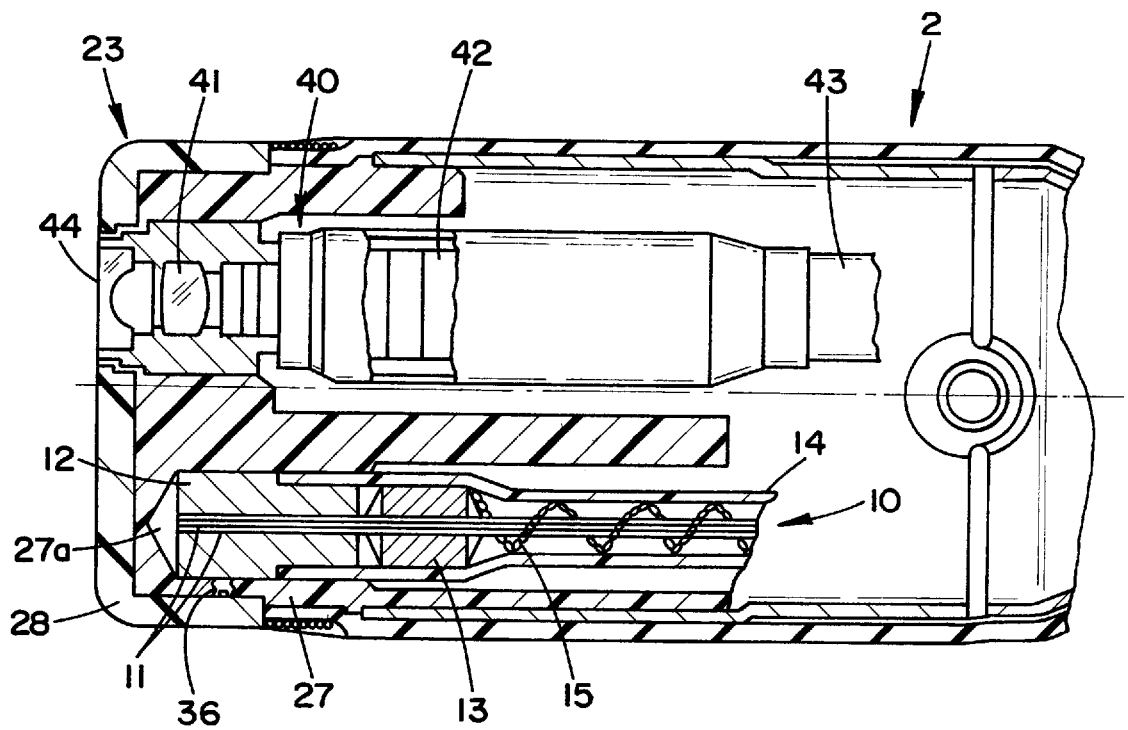
FIG. 2 illustrates a sectional view of a distal end structural section of an insertion section according to the first embodiment of the present invention.

As shown in FIG. 2, the above-mentioned distal end structural section 23 includes an observation optical system 40, the insertion form detecting probe 10 and an air/water supply nozzle (not shown) that are fixed in the main body 27. The observation optical system 40 includes an illumination optical system (not shown), a treating instrument insertion channel, an objective lens 41, a CCD 42, and an observation window 44. The main body 27 is made of such nonmetallic material as plastic so that the output of the magnetic field is not weakened in a coil 13 (described later) of the insertion form detecting probe 10. Also a protective cover 28 covers the main body 27 for protection.

Figure 3:
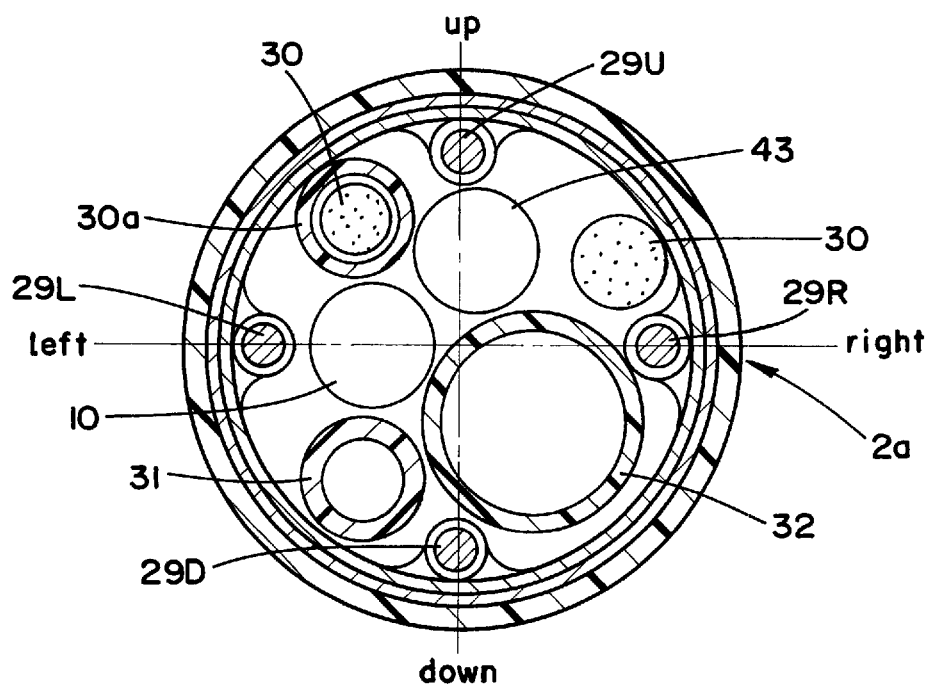
FIG. 3 illustrates a sectional view of the contents arranged inside an insertion section according to the first embodiment of the present invention.
Figure 4:
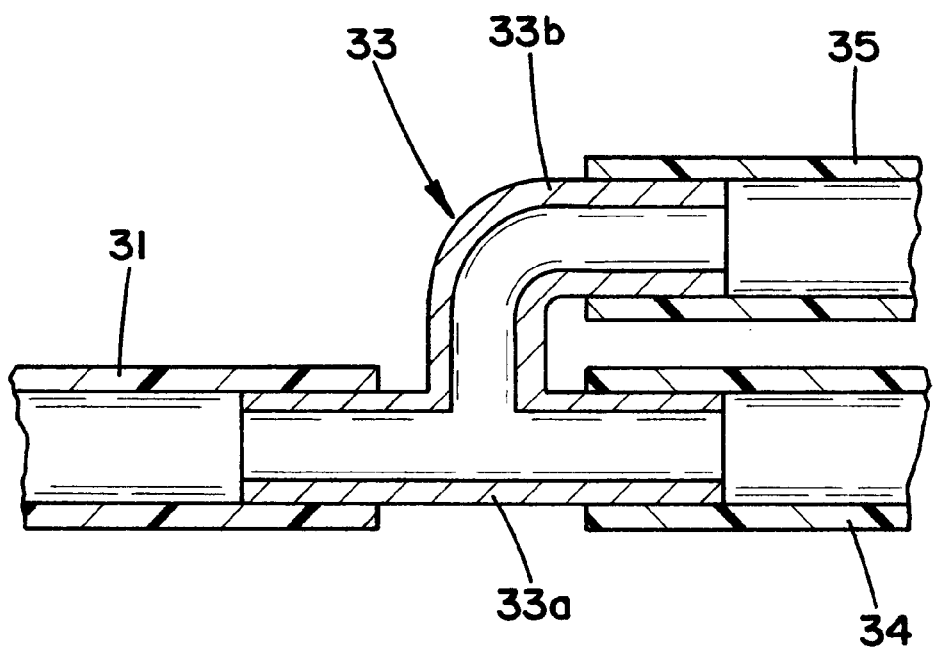
FIG. 4 illustrates a sectional view of an air/water supply channel branch member according to the first embodiment of the present invention.

As shown in FIG. 3, an insertion section 2a of the endoscope 2 includes such contents inside as the insertion form detecting probe 10, an image signal transmitting cable 43, four angle wires 29U, 29D, 29L and 29R, two light guide fiber bundles 30, an air/water supply channel tube 31 communicating with the air/water nozzle, a treating instrument insertion channel tube 32. The four angle wires 29U, 29D, 29L and 29R are located at respectively up and down and right and left positions inside of the insertion section 2a. The image signal transmitting cable 43 extends from the CCD 42 and transmits an image signal to the operating section 2b.

Each distal end portion of the above angle wires 29U, 29D, 29L and 29R is fixed to the distal end portion of the curving section 22. Each proximal end portion of the above angle wires 29U, 29D, 29L and 29R extends toward the operation section 2b and is connected to a curving operation device (not shown) provided inside of the operation section 2b. The angle wires 29U, 29D, 29L and 29R are respectively pulled and operated as is known in the art, so that the curving section 22 is curved in a desired direction.

Distal end portions of the two light guide fiber bundles 30 are arranged so as to face the inner side of two illumination windows provided in the distal end structural section 23. Proximal end portions of the two light guide fiber bundles 30 extend through the inside of the operation section 2b and the universal cord 2c into the connector 24. In this configuration, the light from the light source 3a is incident on an end surface of the light guide fiber bundle 30 provided in the connector 24, transmitted through the light guide fiber bundle 30, and outwardly through an illumination window.

The image signal transmitting cable 43 is connected to the endoscope controller 3 at the proximal end portion, through the operation section 2b and the universal cord 2c and the connector 24 and the first connecting cable 25. On the observation with the endoscope, an optical image is focused on an imaging face of the CCD 42 through the observation window 44 and the objective lens 41. The focused optical image is photoelectrically converted into an electrical signal. This electrical signal is then transmitted through the image signal transmitting cable 43 and the first connecting cable 25, to the endoscope controller 3. The electrical signal is then converted into an image signal in a signal processor and displayed as an endoscope observation image on the observation monitor 3c.

The distal end portion of the air/water supply channel tube 31 is connected to the air/water supply nozzle. The proximal end portion of the air/water supply channel tube 31 is connected to an air/water supply channel branch member 33 (hereinafter referred to as the channel branch member) shown in FIG. 4 at a predetermined position in the insertion section 2a.

The channel branch member 33 comprises a first pipe member 33a being a linear metal pipe and a second pipe member 33b being a metal pipe bent at 90°. One end of the second pipe member 33b is connected to the middle portion of the first pipe member 33a to make fluid communication possible. The direction of an end portion of the second pipe member 33b near another end is substantially parallel to the axial direction of the first pipe member 33a.

An air supply tube 34 is mounted to a proximal end portion of the first pipe member 33a. A water supply tube 35 is mounted to the proximal end portion of the second pipe member 33b. Therefore, the channel branch member 33 enables the air supply tube 34, the water supply tube 35, and the air/water supply tube 31 to communicate with one another. The air supply tube 34 and the water supply tube 35 run through the operation section 2b and the universal cord 2c. The proximal end of the air supply tube 34 and the water supply tube 35 are in the connector 24.

The distal end portion of the treating instrument insertion channel tube 32 is connected to and communicates with a treating instrument insertion channel hole (not shown) formed in the main body 27. The proximal end portion of the treating instrument insertion channel tube 32 is connected to and communicates with a treating instrument insertion opening (not shown) provided in the operation section 2b.

Among the two light guide fiber bundles 30 inserted into the insertion section 2a, the circumference of the one which is adjacent to the insertion form detecting probe 10, is covered with soft protective tube 30a. The protective tube 30a covers the circumference of the light guide fiber bundle 30 from it's distal end to the middle of it's whole length that elongates throughout the insertion section 2a. Therefore, a shoulder portion 30b (shown in FIG. 6), having a step shape, is formed at the distal (proximal?) end portion of the protective member 30a on the one light guide fiber bundle 30 proximate to the form detecting probe.

Figure 5:
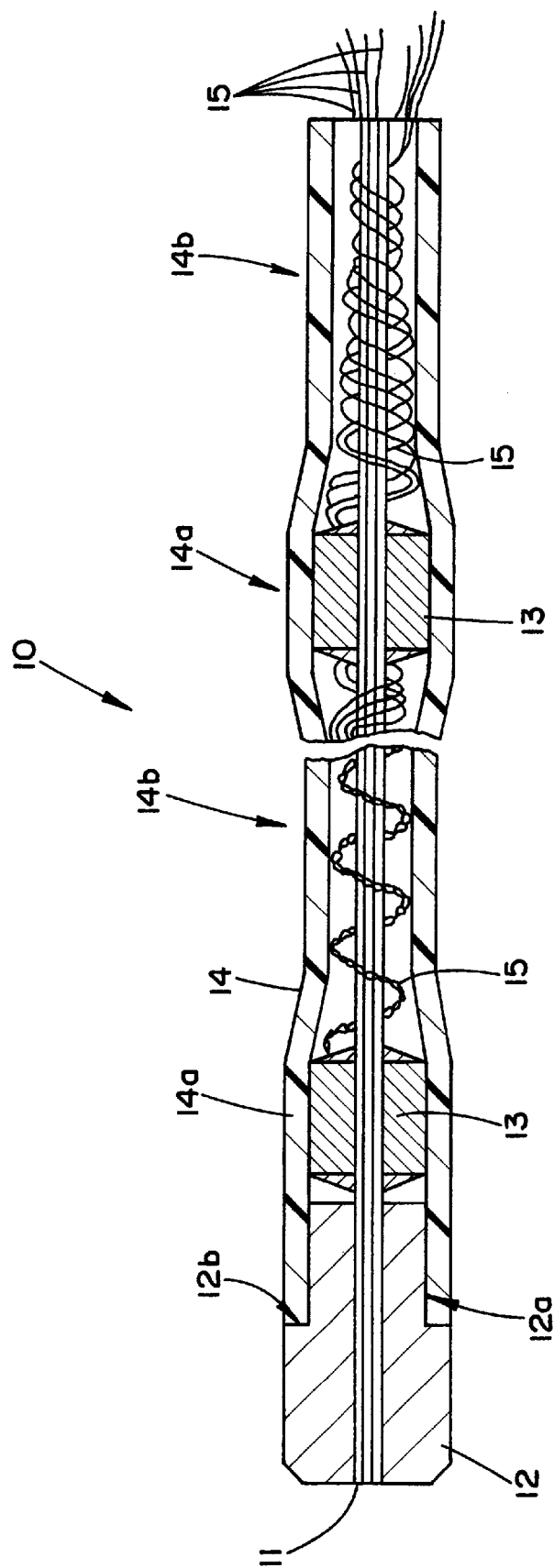
FIG. 5 illustrates a sectional view of an insertion form detecting probe according to the first embodiment of the present invention.

The configuration of insertion form detecting probe 10 is now explained with reference to FIGS. 2 and 5.

As shown in the figures, the insertion form detecting probe 10 comprises a core wire 11 provided at the central axis, a distal end member 12 provided at the distal end portion of the core wire 11, and a plurality of magnetic-field generating coils (hereinafter referred to as coils) 13, and an elongate armor tube 14. Each of the coils 13 are located at predetermined intervals around the core wire 11. The coils 13 are also fixed to the core wire 11, for example by an adhesive. Each coil generates a desired magnetic field. Furthermore, the armor tube 14 is made of such soft heat shrinkage tube as PFA, FEP, PTFE and the like for covering each coil 13 and the core wire 11. The proximal end portion of the distal end member 12 includes a concave portion 12a in which the distal end portion of the armor tube 14 is provided and an abutment face 12b at which the distal end face of the armor tube 14 abuts. The distal end member 12 is fixed to the main body 27.

The core wire 11 is formed by bending and bundling one or plurality of fibers such as Kevlar (a brand name), a polyamide fiber Nylon (a brand name), silk, a poly-arylate fiber Vectran(a brand name) or the like.

Figure 6:
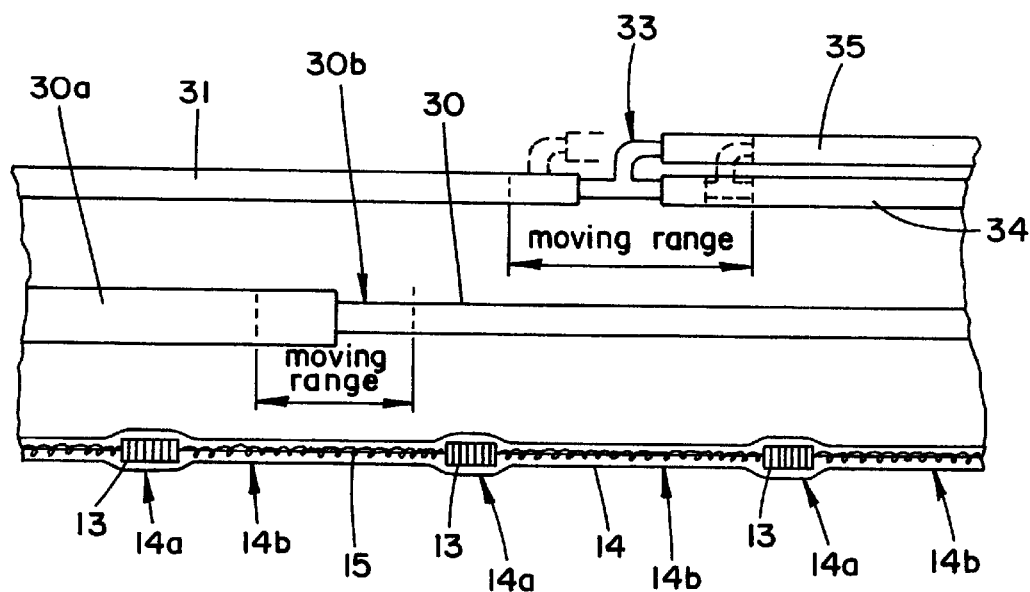
FIG. 6 illustrates a view explaining the relation between an insertion form detecting probe and contents in the longitudinal direction of an insertion section according to the first embodiment of the present invention.

Each of the coils 13 is located at predetermined positions as is shown in FIG. 6, and has a certain relational position with some large parts of the contents and the shoulder portion 30b. One example is positioning each coil 13 along almost the whole length of the insertion section 2a of the endoscope 2 at almost equal intervals. The coil 13 closest to the distal end of the insertion section 2a is desirably positioned as close to the distal end member 12 as possible.

Two signal wires extend out from each coil 13. The signal wires 15 are twisted together to improve the Electromagnetic Compatibility. The signal wires 15 have, for example, Cu—Ag alloy core wire covered with outer protection layer and have good durability for repeated bending.

The outer layer of the signal wire 15 preferably varies in color for each coil 13 so that one can identify a signal wire 15 extending out of a coil 13 among a plurality of coils 13. Therefore, the relation between a signal wire 15 and a coil 13 can be recognized, even if a plurality of signal wires 15 extend together out of the proximal side of the armor tube 14.

The armor tube 14 includes a first covering portion 14a and a second covering portion 14b. The first covering portion 14a is a portion which covers the coil 13. The second covering portion 14b is a portion which covers the signal wire 15. That is, the second covering portion 14b covers the portion between coils 13 and portion from the surface of the coil 13 closest to the proximal end of the insertion section 2a to the proximal end of the core wire 11. The cross-sectional area of the second covering portion 14b is smaller than that of the first covering portion 14a. The cross-sectional area herein is defined as the area of cross-section in which the first and second covering portions 14a and 14b are cut off in the perpendicular direction to the longitudinal direction of the insertion form detecting probe 10.

The distal end member 12, which is a distal end portion of the insertion form detecting probe 10, is fixed by a screw 36 at a concave 27a formed in the main body 27. Then the coils 13 are located at predetermined intervals. As shown in FIG. 6, therefore, the channel branch member 33 is located so as not to interfere with coils 13. Furthermore, the shoulder portion 30b of the protective tube 30a of the protecting the light guide fiber bundle 30 is located so as not to interfere with the coils The positions of the channel branch member 33 and the shoulder portion 30b of the protective tube 30a move forward and backward according to curving forms of the curving section 22 and the flexible tubular section 21 inserted into the body cavity. Therefore, the interval between two coils 13 is predetermined in consideration of the moving ranges of the channel branch member 33 and the shoulder portion 30b. This prevents the coils 13 from interfering with the channel branch member 33 and the shoulder portion 30b.

The operation of the above-mentioned endoscope system will now be explained.

The antenna 4b detects the magnetic field generated by each coil 13 of the insertion form detecting probe 10 during an endoscopy. A signal detected by the antenna 4b is output to the endoscope form detecting apparatus 4 and converted into image data by an image signal processor (not shown) and then output to the form displaying monitor 4a.

On a screen of the form displaying monitor 4a, detected positions of the plurality of coils 13 are displayed on the basis of the magnetic field generated from the coils 13 in the insertion form detecting probe 10. For example, detected positions of all coils 13 are displayed by corresponding dots. The reconstructed form of the insertion section 2a during insertion is displayed by connecting the dots representing the detected position of coils 13. The displayed information enables more accurate operation of the insertion section 2a being inserted into the body.

The diameter of the insertion form detecting probe 10 is smaller at the covering portion 14b where the signal wire 15 is covered, and so is the filling rate. This results in friction resistance among the contents being, reduced therefore, the contents may move smoothly around the second covering portion 14b.

Because of this, in the endoscope system according to the embodiment, contents damage due to excessively compressing or pulling forces can be prevented and the durability of the contents is improved.

The flexibility of the insertion section is also superior to those of the prior art since the armor tube 14 and the core wire 11 and the signal wire 15 are provided between coils of the insertion form detecting probe 10. When the insertion section 2a is curved, therefore, strongly pressing the other contents is prevented. Therefore the durability of the contents may improve.

In this embodiment, those skilled in the art will appreciate that the closer to the distal end, the less the number of signal wires 15. Therefore, the closer to the distal end of the second covering portion 14b of insertion form detecting probe 10 is, the smaller the outer diameter thereof can be. The filling rate of contents at the distal end portion is lower than at the proximal end portion, so that contents can move more smoothly at the distal end. Additionally, since the elastic force of the signal wires 15 is reduced as the distal end of the insertion section 2a is closed, the flexibility of the insertion section 2a increases as the distal end of the insertion section 2a is closed. The durability of contents improves at the curving section 22 wherein the endoscope 2 curves most acutely.

As shown in FIG. 6, the insertion form detecting probe 10 is constituted so that each shoulder portion of the first covering portion 14a and the second covering portion 14b can be apart from the shoulder portion 30b of the protective tube 30a and the channel branch member 33. The moving range of the channel branch member 33 shown in FIG. 6 is also considered in the constitution described above. Contents can smoothly move without the interruption by the shoulder portion, so that the durability of contents may improve.

The protective tube 30a can be used as not only the light guide fiber bundle 30 but also the image signal transmitting cable 43, and the air/water supply channel tube 31.

In case that the protective tube 30a is used as a protective tube for the image signal transmitting cable 43, or the air/water supply channel tube 31, each shoulder portion of the protective tube for the image signal transmitting cable 43, and the air/water supply channel tube 31 is disposed between the first covering portion 14a and the second covering portion 14b as well as the shoulder portion 30b of the protective tube 30a. Also, each shoulder portion of the protective tubes for the image signal transmitting cable 43, and the air/water supply channel tube 31 is disposed apart from the first covering portion 14a and the second covering portion 14b.

On the basis of the above explained constitution, the contents can move smoothly without the interruption by the shoulder portion of the first covering portion 14a and the second covering portion 14b, so that the durability of contents may improve.

Figure 7:
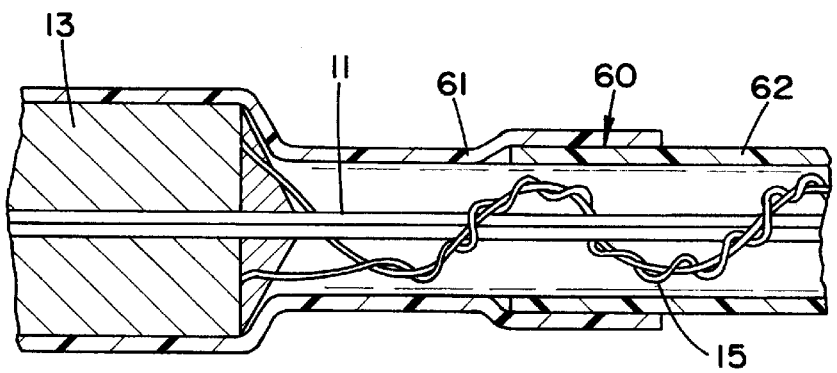
FIG. 7 illustrates a sectional view showing another constitution of an armor tube according to the first embodiment of the present invention.

In the previously described embodiment, the armor tube 14 consists of a single tube. However, a plurality of tubes may be joined together for forming the armor tube 14. For example, a first armor tube 61 and a second armor tube 62 may be joined together as shown in FIG. 7. A female opening is provided at one end portion of the first armor tube 61. The second armor tube 62 comprises a male opening which is inserted into the female opening of the first armor tube 61 tightly. The first and second armor tubes 61, 62 are joined together by an adhesive 60 as the male opening is inserted into the female opening. At the jointed part, the first armor tube 61 has the same or smaller diameter than the diameter at the part covering the coils 13.

Constituting the armor tube using a plurality of tubes jointed together makes the assembly of the form detecting probe 10 easier. If single armor tube 14 covers the coil 13 and the signal wire 15, the length of the armor tube 14 must be longer than that of the first armor tube 61 or the second armor tube 62. In this case, the insertion of the coils 13 and the signal wire 15 can be difficult. The armor tube 14 may be buckled when assembled. As shown in FIG. 7, however, these problems are resolved if the armor tube 14 is separately configured. It is easier, therefore, to cover the coils 13 and the signal wires 15 with the armor tube 14. The filling rate of contents at the joint is not high, since the outer diameter at the joint of the armor tubes 61 and 62 is not larger than the outer diameter of the armor tube 14 covering the coil 13. Therefore, the durability of the contents is increased.

In FIGS. 1 to 6, the disclosed insertion form detecting probe 10 has a smaller diameter in portions where the signal wire 15 is running therein, so the contents filling rate of the probe 10 is along the whole length of the insertion section 2a, so the diameter of the endoscope could be reduced. Contents can move more smoothly and higher durability can be obtained than in an armor tube 14 where only a short portion of it has a small diameter.

It is further understood by those skilled in the art that the foregoing description is a preferred embodiment of the present invention and that various changes and modifications may be made in the invention without departing from the spirit and scope thereof.

Figure 8:
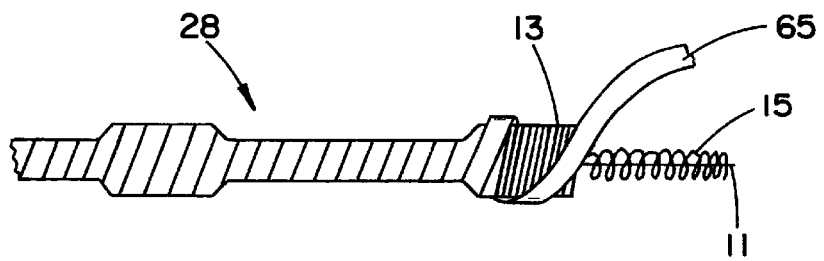
FIG. 8 illustrates a further constitution of an armor tube according to the first embodiment of the present invention.

For example, a sheet armor member 65 may be spirally wound as shown in FIG. 8 instead of the armor tube 14, although the armor tube 14 is used as an armor member in the above embodiment.

In the previously described embodiment, the probe 10 including a plurality of coils 13 for generating the magnetic field is inserted into the body cavity and the antenna 4 for detecting the magnetic field is provided outside the body. A constitution with the contrary function may be used. The probe 10 may comprises magnetic field detecting coils which are used as a magnetic field detecting antenna, meanwhile a device is provided so as to generate the magnetic field. The magnetic field detected by a plurality of coils in the probe is used for operation, so that the form of the insertion section in an endoscope is on the form displaying monitor 4a.

In the previously described embodiment, the second covering portion 14b, where the diameter is smaller than the first covering portion 14a, is located where the filling rate of contents is high. The filling rate average of the whole insertion section is lowered, therefore, and then fewer problems by the content friction occur.

A second embodiment of the present invention is now explained with reference to FIGS. 9–11.

A soft section 79 and a form detecting probe 81 are explained with reference to FIGS. 9 to 11. The soft section 79 contains the form detecting probe 81 as well as an air/water supply tube, a forceps channel, a CCD cable, a light guide fiber, an angle wire for curving a curving section and the like, all of which are not shown. Only the form detecting probe 81 is herein shown for explanation simplification.

Figure 9:
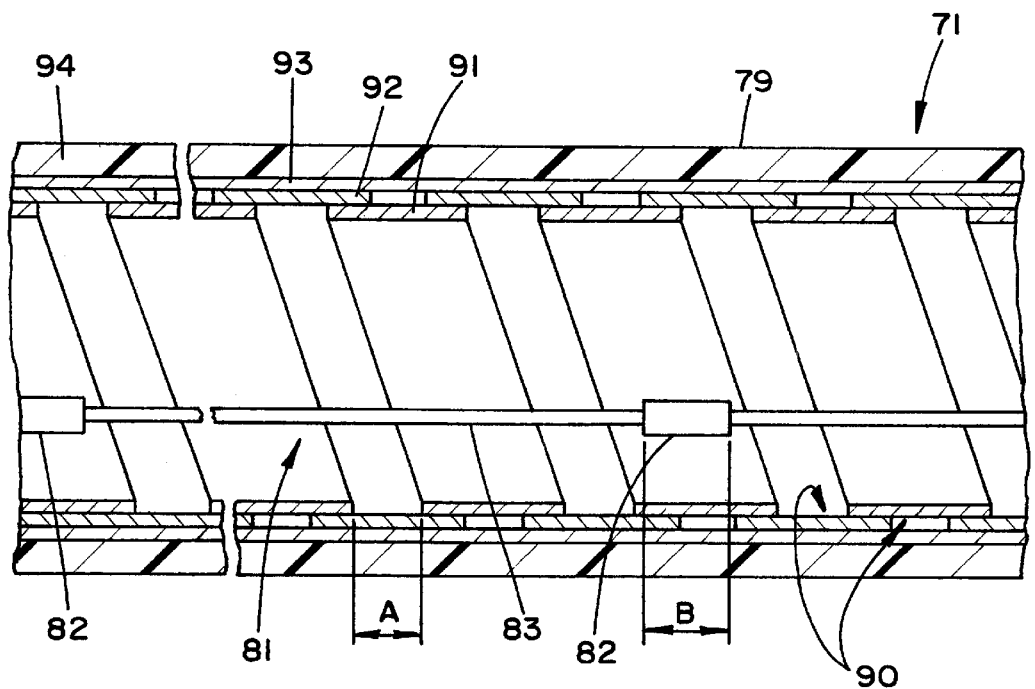
FIG. 9 illustrates a sectional view showing a constitution of a soft section of an insertion section and a form detecting probe according to a second embodiment of the present invention.

As shown in FIG. 9, a plurality of coil portions 82 for generating the magnetic fields are provided along the form detecting probe 81 within an insertion section 71. The coil portions 82 are located at predetermined intervals. Flexible portions 83 whose outer diameter are smaller than that of the coil portion 82 are provided between the coil portions 82.

The soft section 79 of the insertion section 71 comprises from the innermost layer outward, a first spiral tube 91, a second spiral tube 92, braid 93 and an outer tube 94 in this order. The first spiral tube 91 is a spirally wound metal tape having gaps 90 between each wind. The second spiral tube 92 is wound in the opposite direction of the first spiral tube 91. The braid 93 comprises metal strands which are net and formed into a tube. The outer tube 94 is formed of a resin member such as polyurethane.

Figure 10:
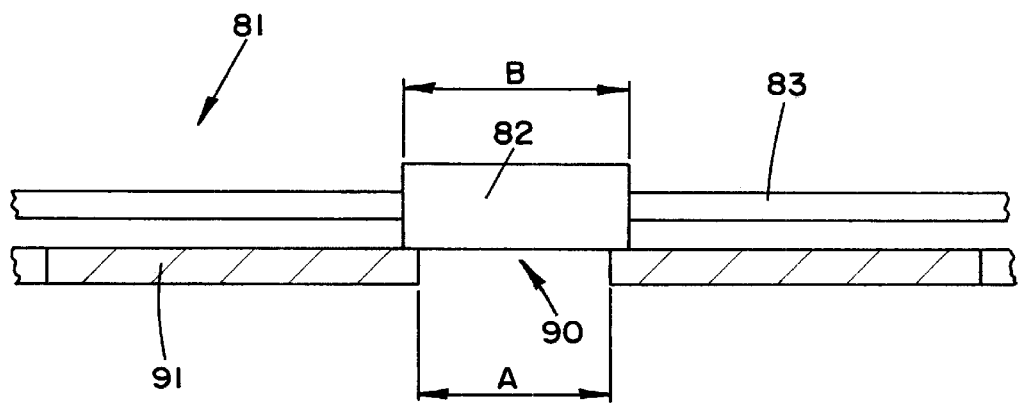
FIG. 10 illustrates the relation between a gap of a soft section and a coil portion of a form detecting probe according to the second embodiment of the present invention.

As shown in FIGS. 9 and 10, the first spiral tube 91 forms the innermost surface of the soft section 79. The first spiral tube 91 also comprises the gaps 90 whose width is A, along the whole length thereof.

The longitudinal length of the coil portion 82 in the form detecting probe 81 is set to B. The length B is longer than the longitudinal width A of the gap 90 in the first spiral tube 91. The relation between A and B is A<B. As shown in FIG. 10, this prevents the coil portion 82 from engaging into the gap 90 of the first spiral tube 91.

In the embodiment, the gap 90 of the first and second spiral tubes 91, 92 has the same width along the total length. However, the width of the proximal gap 90 may be narrowed gradually toward the proximal end than the width of the distal gap 90.

Figure 11:
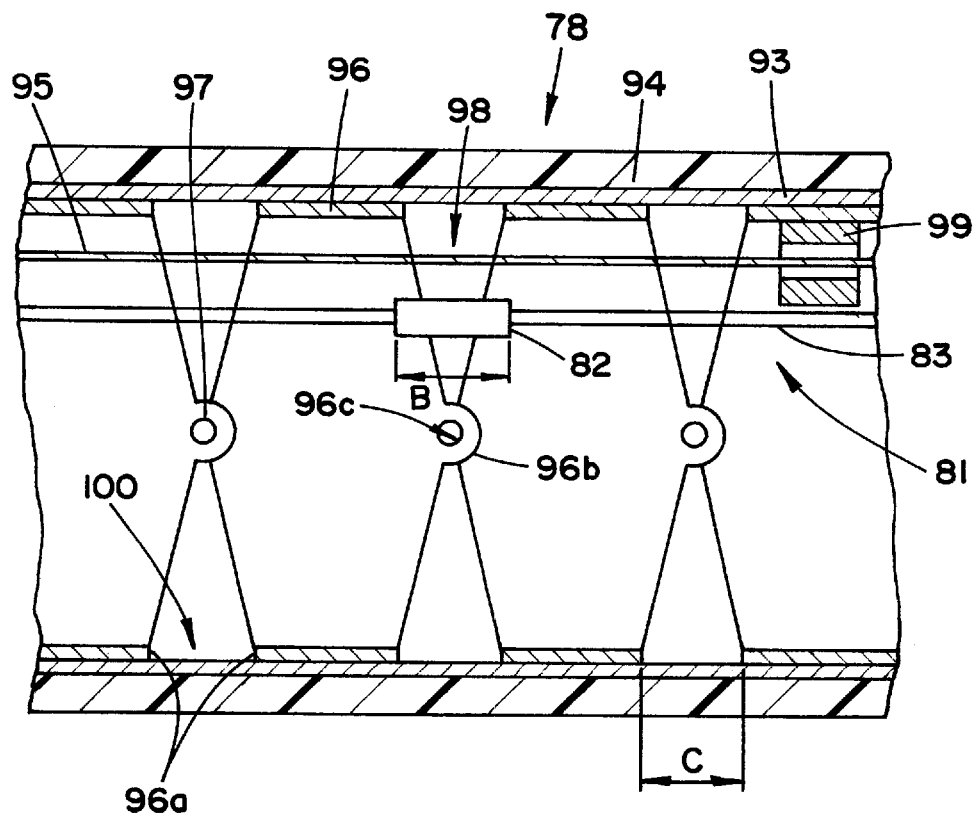
FIG. 11 illustrates a sectional view showing the relation between a curving section of an insertion section and a form detecting probe according to the second embodiment of the present invention.

With reference to FIG. 11, a curving section 78 and the form detecting probe 81 are explained now. The curving section 78 also includes an air/water supply tube, a forceps channel, a CCD cable, a light guide fiber and the like, all of which are not shown. Only the form detecting probe 81 and one angle wire 95 for curving the curving section 78 are herein shown for explanation simplification.

As shown in FIG. 11, the curving section 78 comprises a curving tube 98, the braid 93 covering the curving tube 98 and the outer tube 94. The curving tube 98 comprises metal short cylindrical tubular bodies 96 which form the innermost surface. The bodies 96 are assembled rotatably by a pivot 97.

A longitudinal gap 100 is the gap between edge portions 96a of the adjacent bodies 96, as shown in FIG. 11. The length of gap 100 is set to C which is smaller than the longitudinal length B of the coil portion 82. The relation between the gap length C and the length B is C<B. This prevents the coil portion 82 from engaging into the gap 100 between the end portions 96a of adjacent bodies 96.

The angle wire 95 is provided into the curving section 78 so as to make the curving section 78 curve. The angle wire is inserted though a wire receiving member 99. The wire-receiving member 99 is brazed to a predetermined position on the inner surface of predetermined short cylindrical tubular body 96. The distal end portion of the angle wire 95 is fixed to the distal end portion 77 of the insertion section 71. The proximal end portion of the angle wire 95 is fixed to a curving knob (not shown) located in the operation section 2b.

In the curving tube 98, the pivots 97 of the tubular body 96 are inserted into through-holes 96c formed in connecting sections 96b of the adjacent tubular bodies 96, so that the tubular bodies 96 can rotatably move. In FIG. 11, the pivots are mounted in horizontal direction, so the curving section 78 may move in the vertical direction. Each tubular body 96 is also rotatably connected to the adjacent tubular body 96 at a position rotated by 90 degrees to allow the curving section 78 to also move horizontally. The assembly of tubular bodies 96 with the pivot 97 enables the distal end portion of the curving section 78 to face toward a desired direction vertically and/or horizontally.

As mentioned above, the longitudinal length of the coil portion is set longer than the longitudinal gap length between the edge portions of adjacent tubular bodies as well as the gap width of the first spiral tube. Therefore, the coil portion can be prevented from engaging into a gap between tubular bodies and a gap in the first spiral tube.

This solves the movement problems of the form detecting probe due to coil portion engaging into a gap. Also the potential damage of the form detecting probe decreases so that the durability of the endoscope greatly improves.

A third embodiment is now explained with reference to FIGS. 12 and 13.

Figure 12:
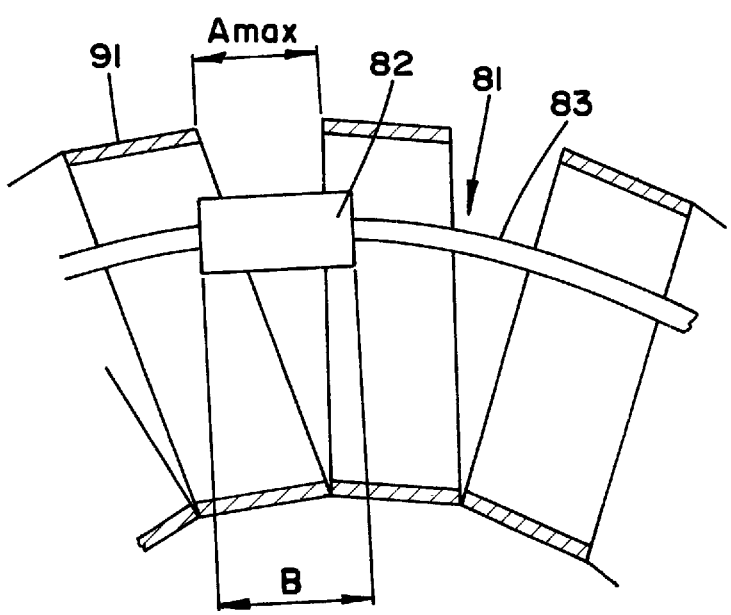
FIG. 12 illustrates the relation between a first spiral tube in a soft section which is in the curving state and a coil portion of an insertion form detecting probe according to a third embodiment of the present invention.

As shown in FIG. 12, when the soft section 79 curves at the smallest curvature, the first spiral tube 91 has no gap therebetween on the inner side. On the other hand, the outer side of the first spiral tube 91 has the gap 90 having largest width Amax. In this embodiment, the relation between the largest width Amax and the longitudinal length B of the coil portion 82 is Amax<B.

Figure 13:
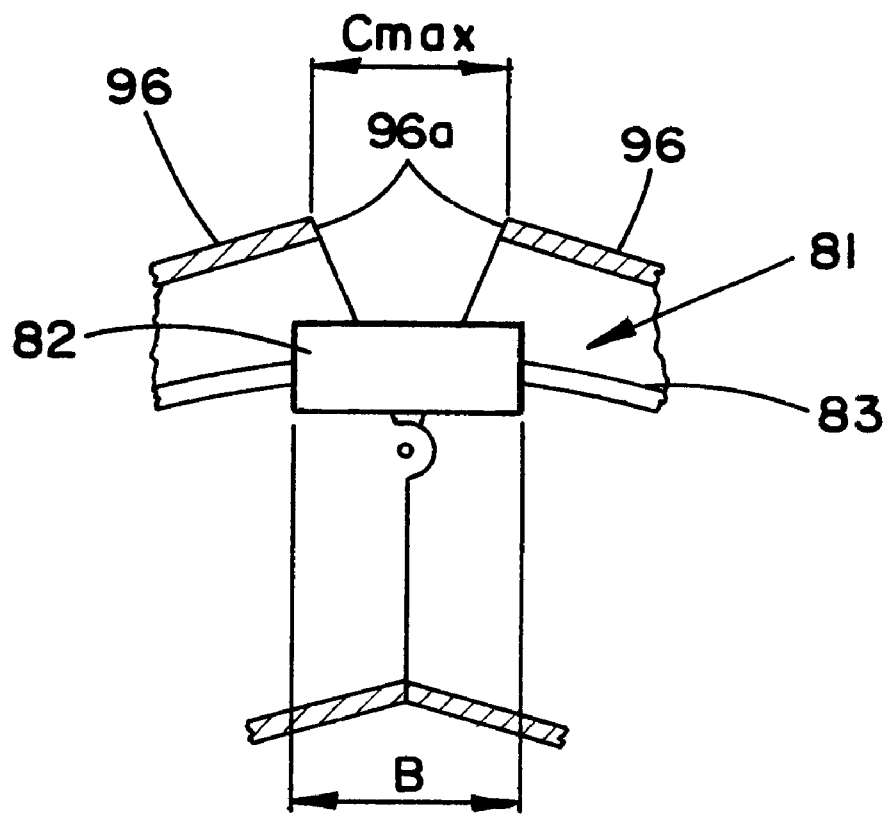
FIG. 13 illustrates the relation between a curving section in the curving state and a form detecting probe according to the third embodiment of the present invention.

As shown in FIG. 13, when the curving section 78 curves at the smallest curvature, the edge portions 96a contact to that of the adjacent tubular bodies 96 in inner side of the curve. At this time, the longitudinal gap between the edge portions 96a of adjacent tubular bodies 96 on the outer side of the curving tube 98 is the largest and having length Cmax.

In this embodiment, the relation between the largest length Cmax and the longitudinal length B of the coil portion 82 is Cmax<B.

This constitution prevents the coil portion 82 from engaging into the gap 90 of the first spiral tube 91 and the gap between the edge portions 96a of adjacent tubular bodies 96 in the curving tube 98. Even if the curving section 78 and the soft section 79 curve tightly and the coil portion 82 abuts the first spiral tube 91 and the curving tube 98, engagement is prevented. As a result, the form detecting probe can move smoothly in the longitudinal direction when curving is operated. And the durability of the form detecting probe and other contents is improved.

There is a difference in diameter between the coil portion 82 and the flexible portion 83 of the form detecting probe 81. Even if the positions of the coil portion 82 and contents are adjusted properly, the coil portion 82 may repeatedly abut the wire receiving member 99, accordingly. That is, the armor tube as an armor member of the form detecting probe 81 may be deteriorated over time to make holes. As a consequence, a copper wire forming the coil portion 82 may be broken.

The following fourth embodiment, therefore, will explain the coil portion of the form detecting probe which can be durable to withstand the engagement of the wire receiving member 99. The fourth embodiment will be described with reference to FIGS. 14 to 17.

Figure 14:
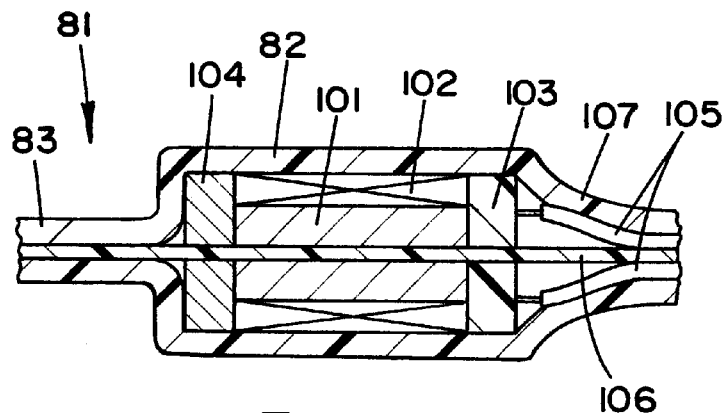
FIGS. 14 to 16 illustrate sectional constitutions of a coil portion of a form detecting probe.

As shown in FIG. 14, the coil portion 82 in this embodiment comprises a core portion 101, a coil 102, a substrate 103 and a protective member 104, these are integrally joined by an adhesive. The core portion 101 is formed of magnetic materials such as ferrite and Permalloy. A copper wire is wound around the core portion 101 desired times so as to form the coil 102. The substrate 103 is provided to the proximal portion of the coil 102 and an end of the copper wire is connected thereto. The protective member 104 is provided to the distal end portion of the coil 102. The coil 102, the substrate 103 and the protective member 104 have the same outer diameter.

The signal wire 105 is connected to the substrate 103, for example, by soldering. The proximal end portion of the signal wire 105 connected to each substrate 103 is connected to a form detecting connector (not shown).

A through hole is provided in each center of the protective member 104, the core portion 101 and the substrate 103, preferably through their centers. A connection member 106, provided along the total length of the form detecting probe 81, is fixed to a predetermined position of the hole by an adhesive.

A flexible armor tube 107 covers the protective member 104, the core portion 101, the coil 102, the substrate 103, the signal wire 105 and the connection member 106 along the total length.

The armor tube 107 is a polyolefin heat shrinkage tube, for example. The polyolefin heat shrinkage tube is heated and shrinks, so that the tube almost coheres to contents. Therefore, the outer diameter of the coil portion 82 is larger than the outer diameter of the flexible portion 83 located ahead and behind of the coil portion 82. The armor of the form detecting probe 81 has a difference in diameter. High strength alamido fiber, for example five Kevlar strings, are bundled for forming the connection member 106.

The form detecting probe 81 shown in FIG. 14 includes the substrate 103 and the protective member 104 which have the same outer diameter as that of the coil 102 at both ends of the coil 102. Even if the coil portion 82 repeatedly abuts the end portion of the wire receiving member 99 and the armor tube 107 has a hole, the coil 102 is prevented from directly abutting the wire receiving member 99 so that the durability improves.

Figure 15:
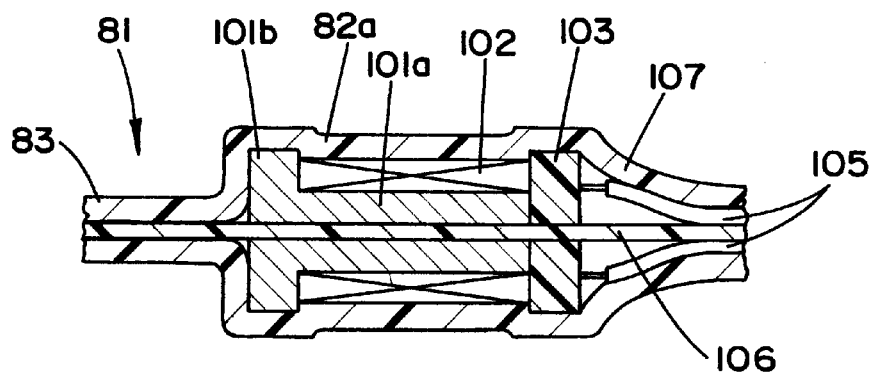

The form detecting probe 81 shown in FIG. 15 comprises a core portion 101a including a flange portion 101b into which the protective member 104 and the core portion 101 are integrated, instead of providing the protective member 104 and the core portion 101 independently. The flange portion 101b and the substrate 103 have larger outer diameters than that of the coil 102.

Each coil portion 82a comprises the core portion 101a, the coil 102 and the substrate 103. The core portion 101a and the flange portion 101b are integrated. The flange portion 101b is arranged at the distal end portion of the core portion 101a and has a larger outer diameter than that of the core portion 101a. A copper wire is wound around the core portion 101a desired times to form the coil 102. The substrate 103 is arranged at the proximal end portion of the coil 102 and connected to the end of the copper wire. The other constitutions are the same as those in FIG. 14. The same reference numerals denote the same elements and a detailed description thereof is omitted.

The core portion 101a including the flange portion 101b does not require the step of fixing the protective member 104 to the core portion 101 by an adhesive. The assembly therefore becomes easier than that of the coil portion 82 shown in FIG. 14.

Additionally, the flange portion 101b and the substrate 103 having the larger outer diameter than that of the coil 102 effectively prevents the coil 102 and the wire receiving member 99 from directly abutting each other. Therefore, the durability of the form detecting probe 81 is improved.

Figure 16:
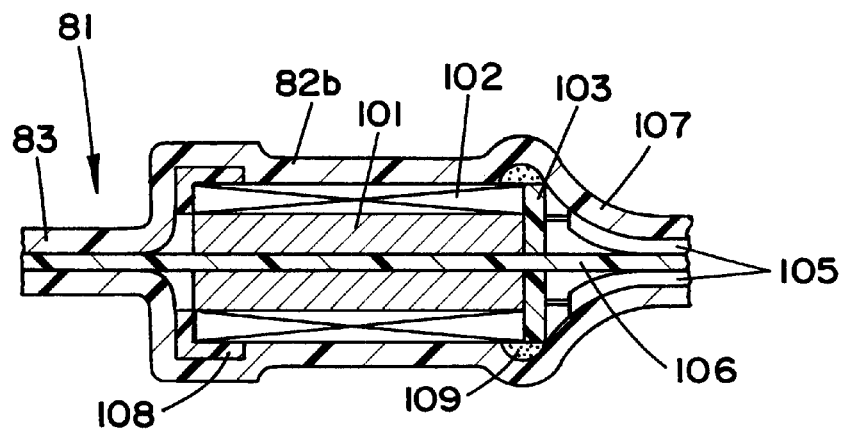

The form detecting probe 81 in FIG. 16 comprises a heat shrinkage tube 108 attached to the distal end side of the coil 102, instead of the protective member 104 shown in FIG. 14. The circumference of the boundary between the substrate 103 and the coil 102 is coated with an epoxy adhesive 109 so that the outer diameter of the coated part is larger than the outer diameter of the coil 102.

The heat shrinkage tube 108 covering the distal end of the coil makes the assembly easier compared with the coil portion 82 of FIG. 14. Furthermore, the coil 102 can be effectively prevented from directly abutting the wire receiving member 99. Therefore, the durability of the form detecting probe 81 is improved.

The outer diameter on the adhesive 109 is larger than the outer diameter of the coil 102. Therefore, the abutment of the wire receiving member 99 and the coil 102 can be effectively prevented, even if the outer diameter of the substrate 103 is smaller than that of the coil 102. The adhesive 109 also reinforces the fixing of the coil 102 and the substrate 103.

Figure 17:
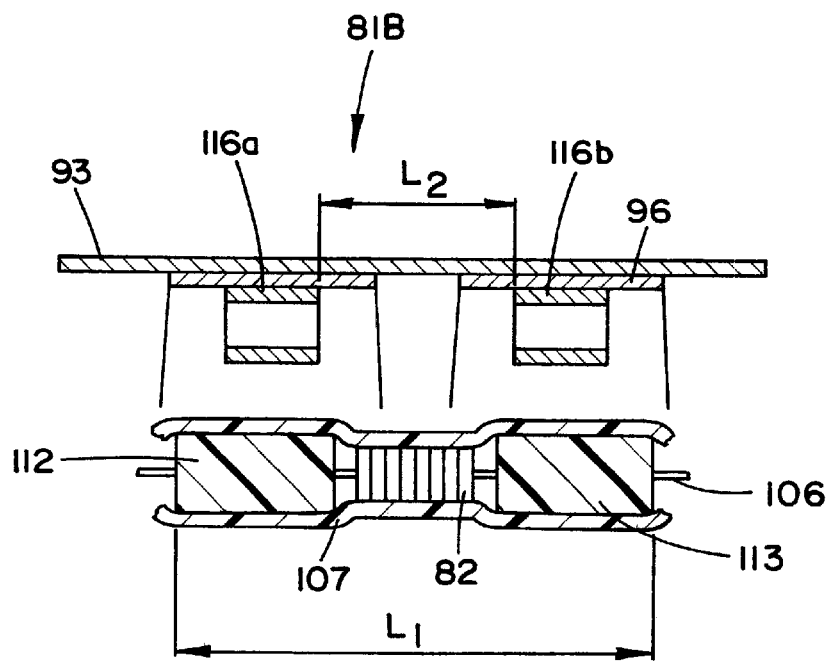
FIG. 17 illustrates a sectional constitution of a form detecting probe.

Other constitutions of the form detecting probe are now explained with reference to FIGS. 17 and 18. As shown in FIG. 17, a form detecting probe 81B comprises flexible members 112 on the distal side and other flexible members 113 on the proximal side of each coil portion 82. L1 is the length from the distal end portion of the flexible member 112 to the proximal end portion of the flexible member 113. L2 is the length from the proximal end portion of a wire receiving member 116a to the distal end portion of a wire receiving member 116b. L3 (not shown) is the length in which the coil portion 82 moves as the form detecting probe 81B axially moves by the curving movement. The relation between L1 and L2, L3 is L1<L2+L3.

The above relation of L1, L2, and L3 prevents the coil portion 82 from abutting the wire receiving members 116a and 116b.

Figure 18:
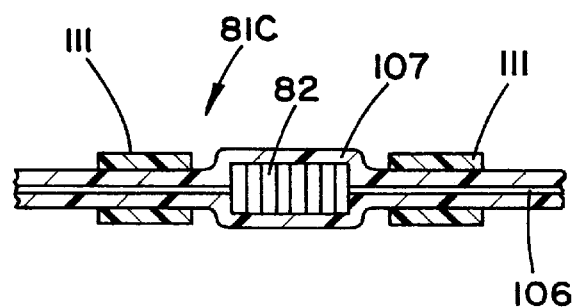
FIG. 18 illustrates another sectional constitution of a form detecting probe.

In FIG. 18, a further constitution of the form detecting probe is explained. A form detecting probe 81C comprises a flexible member 111 outside the armor tube 107.

Since the flexible member 111 can be provided outside the armor tube 107 according to the location of the endoscope contents and the wire receiving member 99, the form detecting probe 81 can be used for a variety of endoscopes.

Figure 19A:
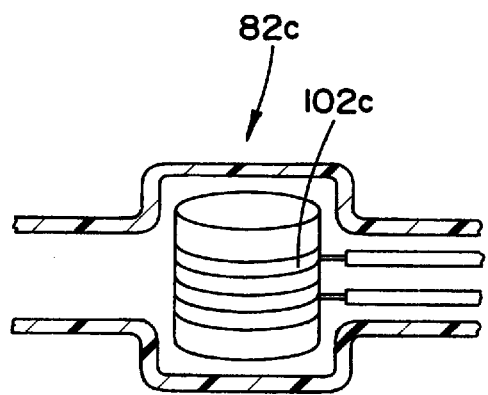
FIGS. 19(a) and 19(b) illustrate a further constitution of a form detecting probe.
Figure 19B:
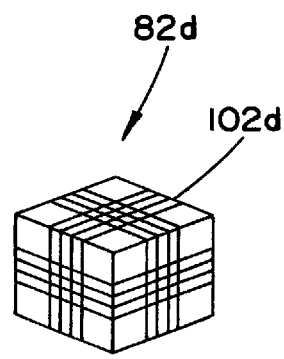

As a preferable configuration of the coil portion of the form detecting probe, the configuration in which cylindrical coils are located in a coaxial way has been described above. However, as shown in FIG. 19(a), coil portion 82c may comprise a cylindrical coil 102c orthogonal to the central axis for obtaining the same effect. Moreover, as shown in FIG. 19(b), a coil portion 82d may comprise a three-axis coil 102d having three orthogonal axes for the same effect.

Figure 20:
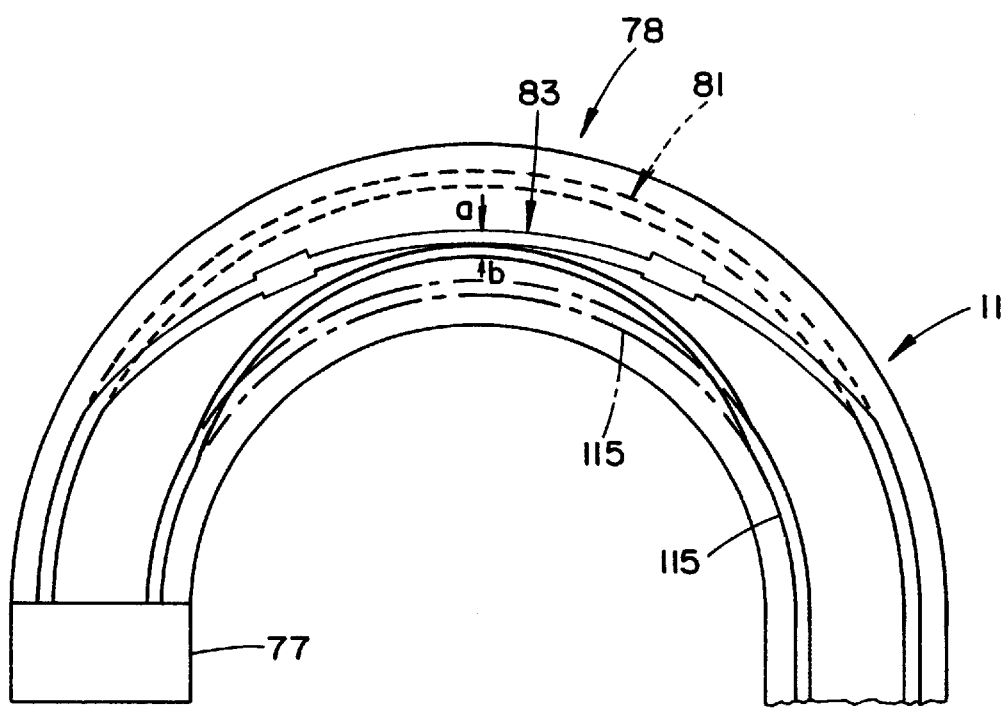
FIG. 20 explains the flexibility of the form detecting probe.

Additionally, the flexible portion 83 of the form detecting probe 81 is more flexible than other contents such as an air/water supply tube. As shown in FIG. 20, when the curving section 78 is curved, the form detecting probe 81 moves inward from the outer dashed line position to the solid line position as indicated by arrow a. On the other hand, an air/water supply tube 115 moves outward from the inner chain line position to the solid line position as indicated by an arrow b, since the tube 115 is formed of a harder member than the flexible portion 83, such as Teflon.

This may result in the form detecting probe 81 and the air/water supply tube 115 to contact each other. Since the flexible portion 83 of the form detecting probe 81 is more flexible than the other contents, however, the flexible portion 83 does not damage the other contents nor will it be damaged by the other contents. The durability improves, accordingly.

It is further understood by those skilled in the art that the foregoing description is preferred embodiments of the present invention and that various changes and modifications may be made in the invention without departing from the spirit and scope thereof.

What is claimed is:

1. An endoscope comprising:
   an insertion section for being inserted into a body cavity; and
   a probe provided inside said insertion section for detecting the form of said endoscope, the probe including a plurality of coil portions arranged in the longitudinal direction of said insertion section of said endoscope, a wire electrically connecting said plurality of coil portions, and a flexible member covering said coil portions and said wire,
      wherein the cross section area of said covered wire is smaller than the cross section area of said covered coil portions.

2. The endoscope according to claim 1, wherein
   said insertion section is a curvable flexible member;
   said insertion section includes a content inside other than said probe;
   said content includes a first section connected to a distal end portion of said insertion section, a second section connected to a proximal end portion of said insertion section which has a larger diameter than said first section, and) a connecting section connecting said first section and said second section;
   said content is arranged along said insertion section and moves in the extending direction of said insertion section according to the curving of said insertion section; and
   said connecting section moves between arbitrary adjacent two of said coil portions so that said arbitrary adjacent two coil portions maintain a non-contact condition when said content moves.

3. The endoscope according to claim 2, wherein
   in said content, said first section includes an air/water supply tube for supplying both air and water, said second section includes an air supply tube and a water supply tube, and said connecting section includes a connector for sending air from said air supply tube and liquid from said water supply tube to said air/water supply tube.

4. The endoscope according to claim 1, wherein
   said insertion section is formed of a curvable flexible member;
   said insertion section includes a content inside other than said probe;
   said content is provided along said insertion section and includes a shoulder portion in the elongated direction;
   said content moves to the elongated direction of said insertion section according to the curving of said insertion section; and
   said shoulder portion moves between said arbitrary adjacent two coil portions so that said arbitrary adjacent two coil portions maintain a non-contact condition when said content moves.

5. The endoscope according to claim 4, wherein
   said content includes at least one of a light guide formed of a bundle of fibers, an image signal transmitting cable, and an air/water supply channel tube, each of which is covered with a protective member from its distal end portion to a desired portion, and wherein an end of said protective member forms said shoulder portion.

6. The endoscope according to claim 1, further comprising:
   a fixing member on the distal end portion of said insertion section for fixing said probe.

7. The endoscope according to claim 6, further comprising:
   a distal end member in said probe, fixed to said fixing member, one of said plurality of coil portions being provided close to said distal end member.

8. The endoscope according to claim 1, wherein
   said flexible member covering said coil portions and said wire comprises an elastic tube.

9. The endoscope according to claim 1, wherein
   a plurality of elastic tubes are joined for forming said flexible member covering said coil portions and said wire.

10. An endoscope according to claim 1, wherein a longitudinal length of said coil portions is longer than a longitudinal width of a gap formed on an inner surface member consisting of an innermost surface of said insertion section.

11. The endoscope according to claim 10, wherein
    said inner surface member is a soft section comprising a spiral tube formed of a spirally wound tape; and
    the longitudinal length of said coil portions is longer than a longitudinal width of a gap between successive windings of said spiral tube.

12. The endoscope according to claim 10, wherein
    said inner surface member is a curving tube in which short cylindrical tubular bodies, which are part of a curving section of said insertion section, are rotatably provided in a row arrangement;

and the longitudinal length of said coil portions is longer than a longitudinal gap length between edge portions of adjacent said tubular bodies forming said curving tube.

13. The endoscope according to claim 11, wherein the longitudinal length of said coil portions is set longer than the longitudinal largest out side gap length between successive windings of said spiral tube when said insertion section is curved.

14. The endoscope according to claim 12, wherein the longitudinal length of said coil portions is set longer than a longitudinal largest outside gap length between edge portions of adjacent said bodies when said insertion section is curved.

15. An endoscope according to claim 1, wherein a longitudinal length of said covered coil portions is longer than a longitudinal length of a gap formed on an inner surface member consisting of an innermost surface of said insertion section.

16. An endoscope system comprising:
the endoscope according to claim 1;
a device located outside the body, for detecting the magnetic field generated from said probe or for generating the magnetic field to be detected by said probe;
a processor for calculating the form of said endoscope insertion section on the basis of the magnetic field detected by said probe or said outside device; and
a monitor for displaying the form of said endoscope insertion section on the basis of a result from said processor calculation.

17. The endoscope system according to claim 16, further comprising:
a fixing member on the distal end portion of said insertion section for fixing said probe.

18. The endoscope system according to claim 17, further comprising:
a distal end member in said probe, fixed to said fixing member, one of said plurality of coil portions provided close to said distal end member.

19. The endoscope system according to claim 16, wherein said flexible member covering said coil portions and said wire comprises an elastic tube.

20. The endoscope system according to claim 16, wherein a plurality of elastic tubes are joined for forming said flexible member covering said coil portions and said wire.

21. An endoscope system comprising:
an endoscope having an insertion section for being inserted into the body cavity; and a probe provided inside said insertion section for detecting the form of said endoscope, the probe including a plurality of coil portions arranged in the longitudinal direction of said insertion section of said endoscope, a wire electrically connecting said plurality of coil portions and having a cross section area being smaller than that of said coil portions, and a flexible member covering said coil portion and said wire;
a device located outside the body, for detecting the magnetic field generated from said probe or for generating the magnetic field to be detected by said probe;
a processor for calculating the form of said endoscope insertion section on the basis of the magnetic field detected by said probe or said outside device; and
a monitor for displaying the form of said endoscope insertion section on the basis of a result from said processor calculation, wherein
said insertion section is formed of a curvable flexible member;
said insertion section includes a content inside other than said probe;
said content includes a first section connected to a distal end portion of said insertion section, a second section connected to a proximal end portion of said insertion section which has a larger diameter than said first section, and a connecting section connecting said first section and said second section;
said content is arranged along said insertion section and moves to elongated direction of said insertion section according to the curving of said insertion section; and
said connecting section moves between arbitrary adjacent two of said coil portions so that said arbitrary adjacent two coil portions keep non-contact condition when said content moves.

22. The endoscope system according to claim 21, wherein in said content, said first section includes an air/water supply tube for supplying both air and water, said second section includes an air supply tube and a water supply tube, and said connecting section includes a connector for sending air from said air supply tube and liquid from said water supply tube to said air/water supply tube.

23. An endoscope system comprising:
an endoscope having an insertion section for being inserted into the body cavity; and a probe provided inside said insertion section for detecting the form of said endoscope, the probe including a plurality of coil portions arranged in the longitudinal direction of said insertion section of said endoscope, a wire electrically connecting said plurality of coil portions and having a cross section area being smaller than that of said coil portions, and a flexible member covering said coil portions and said wire;
a device located outside the body, for detecting the magnetic field generated from said probe or for generating the magnetic field to be detected by said probe;
a processor for calculating the form of said endoscope insertion section on the basis of the magnetic field detected by said probe or said outside device; and
a monitor for displaying the form of said endoscope insertion section on the basis of a result from said processor calculation, wherein
said insertion section is formed of a curvable flexible member;
said insertion section includes a content inside other than said probe;
said content is provided along said insertion section and includes a shoulder portion in the elongated direction;
said content moves to the elongated direction of said insertion section; and
said shoulder portion moves between said arbitrary adjacent two coil portions so that said arbitrary adjacent two coil portions maintain a non-contact condition when said content moves.

24. The endoscope system according to claim 23, wherein
said content is a light guide formed of a bundle of fibers, covered with a protective member from its distal end portion to a desired portion; and
an end of said protective member forms said shoulder portion.

* * * * *